United States Patent
Sakamoto et al.

(10) Patent No.: US 12,031,241 B2
(45) Date of Patent: Jul. 9, 2024

(54) CORE-SHEATH COMPOSITE FIBER FOR ARTIFICIAL HAIR, HEADDRESS PRODUCT INCLUDING SAME, AND PRODUCTION METHOD THEREFOR

(71) Applicant: KANEKA CORPORATION, Osaka (JP)

(72) Inventors: Genta Sakamoto, Osaka (JP); Norikazu Yasutomo, Osaka (JP); Hiroshi Fujinaga, Osaka (JP); Takashi Ogino, Osaka (JP)

(73) Assignee: KANEKA CORPORATION, Osaka (JP)

( * ) Notice: Subject to any disclaimer, the term of this patent is extended or adjusted under 35 U.S.C. 154(b) by 302 days.

(21) Appl. No.: 17/393,698

(22) Filed: Aug. 4, 2021

(65) Prior Publication Data

US 2021/0363667 A1 Nov. 25, 2021

Related U.S. Application Data

(63) Continuation of application No. PCT/JP2020/001147, filed on Jan. 16, 2020.

(30) Foreign Application Priority Data

Feb. 15, 2019 (JP) .................................. 2019-025698

(51) Int. Cl.
*D01F 8/14* (2006.01)
*A41G 3/00* (2006.01)
(Continued)

(52) U.S. Cl.
CPC ............. *D01F 8/14* (2013.01); *A41G 3/0083* (2013.01); *D01D 5/10* (2013.01); *D01F 1/04* (2013.01);
(Continued)

(58) Field of Classification Search
CPC .......................... A41G 3/0083; D10B 2503/08
(Continued)

(56) References Cited

U.S. PATENT DOCUMENTS

| | | | |
|---|---|---|---|
| 2009/0126749 A1* | 5/2009 | Shirakashi | ................ D01F 8/12 132/56 |
| 2019/0090565 A1 | 3/2019 | Miyata et al. | |
| 2020/0024774 A1 | 1/2020 | Yasutomo et al. | |

FOREIGN PATENT DOCUMENTS

| | | |
|---|---|---|
| EP | 1852022 A1 | 11/2007 |
| EP | 3603432 A1 | 2/2020 |

(Continued)

OTHER PUBLICATIONS

International Search Report issued in corresponding International Application No. PCT/JP2020/001147, mailed Mar. 10, 2020, with translation (5 pages).

(Continued)

*Primary Examiner* — Elizabeth M Imani
(74) *Attorney, Agent, or Firm* — Osha Bergman Watanabe & Burton LLP

(57) ABSTRACT

The present disclosure relates to a core-sheath conjugate fiber for artificial hair including a core part and a sheath part, wherein the core-sheath conjugate fiber for artificial hair is a colored fiber, a color difference between the core-sheath conjugate fiber for artificial hair and the core part is 3.0 or more, and a color difference between the core-sheath conjugate fiber for artificial hair and the sheath part is also 3.0 or more. Provided are a core-sheath conjugate fiber for artificial hair capable of realizing deep colors and having a good appearance close to that of human hair, a hair ornament product including the core-sheath conjugate fiber, and a production method.

11 Claims, 1 Drawing Sheet

(51) Int. Cl.
*D01D 5/10* (2006.01)
*D01F 1/04* (2006.01)
*D01F 8/12* (2006.01)

(52) U.S. Cl.
CPC ............ *D01F 8/12* (2013.01); *D10B 2331/02* (2013.01); *D10B 2331/04* (2013.01); *D10B 2401/20* (2013.01); *D10B 2503/08* (2013.01)

(58) Field of Classification Search
USPC .................................................. 428/373, 375
See application file for complete search history.

(56) References Cited

FOREIGN PATENT DOCUMENTS

| | | |
|---|---|---|
| JP | S60173142 A | 9/1985 |
| JP | 2013204180 A | 10/2013 |
| WO | 2006087911 A1 | 8/2006 |
| WO | 2017187843 A1 | 11/2017 |
| WO | WO-2017187843 A1 * | 11/2017 ............... A41G 3/00 |
| WO | 2018179803 A1 | 10/2018 |

OTHER PUBLICATIONS

Written Opinion issued in corresponding International Application No. PCT/JP2020/001147, mailed Mar. 10, 2020 (3 pages).
Office Action issued in corresponding Japanese Patent Application No. 2020-572132, dated Feb. 20, 2024, with translation (10 pages).

* cited by examiner

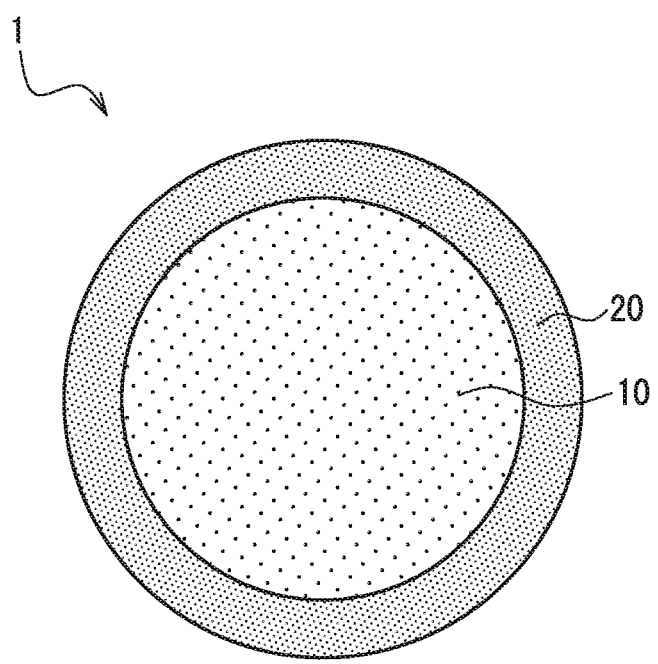

CORE-SHEATH COMPOSITE FIBER FOR ARTIFICIAL HAIR, HEADDRESS PRODUCT INCLUDING SAME, AND PRODUCTION METHOD THEREFOR

This application is a CON of PCT/JP2020/001147, filed Jan. 16, 2020.

TECHNICAL FIELD

One or more embodiments of the present invention relate to a fiber for artificial hair capable of being used as an alternative to human hair, a hair ornament product including the same, and a production method therefor.

BACKGROUND

Conventionally, human hair is used for hair ornament products such as hairpieces, hair wigs, hair extensions, hair bands, and doll hair. However, in recent years, it is becoming difficult to obtain human hair and its price is increasing, and thus there is an increasing demand for fibers for artificial hair capable of being used as an alternative to human hair. Examples of synthetic fibers that can be used as fibers for artificial hair include acrylic-based fibers, vinyl chloride-based fibers, vinylidene chloride-based fibers, polyester-based fibers, polyamide-based fibers, and polyolefin-based fibers.

In particular, a core-sheath conjugate fiber whose core part contains polyester and sheath part contains polyamide has been developed as a fiber for artificial hair having a touch close to that of human hair and having satisfactory durability and heat resistance (Patent Document D.

PATENT DOCUMENT

Patent Document 1: WO 2017/187843

However, the core-sheath conjugate fiber for artificial hair described in Patent Document 1 is problematic in that the appearance is poorer than that of human hair due to its monochromatic and monotonous color. Furthermore, even when various conjugate fibers with different colors are used in a mixed manner for a hair ornament product, the fibers each have a monochromatic color, and thus it is difficult to obtain an appearance close to that of human hair, and, furthermore, it is necessary to produce and mix a plurality of various fibers with different colors, which requires additional steps, that is, there is still room for improvement.

SUMMARY

In order to address the above, one or more embodiments of the present invention provide a core-sheath conjugate fiber for artificial hair capable of realizing deep colors and having a good appearance close to that of human hair, a hair ornament product including the same, and a production method therefor.

In one or more embodiments, the present invention relates to a core-sheath conjugate fiber for artificial hair including a core part and a sheath part, wherein the core-sheath conjugate fiber for artificial hair is a colored fiber, a color difference between the core-sheath conjugate fiber for artificial hair and the core part is 3.0 or more, and a color difference between the core-sheath conjugate fiber for artificial hair and the sheath part is also 3.0 or more.

In one or more embodiments, the present invention relates to a hair ornament product including the core-sheath conjugate fiber for artificial hair.

Furthermore, in one or more embodiments, the present invention relates to a production method for the core-sheath conjugate fiber for artificial hair, including a step of melt spinning a core part resin composition and a sheath part resin composition, using a core-sheath conjugate nozzle.

According to one or more embodiments of the present invention, it is possible to provide a core-sheath conjugate fiber for artificial hair capable of realizing deep colors and having a good appearance close to that of human hair, and a hair ornament product.

Furthermore, according to the production method of one or more embodiments of the present invention, it is possible to obtain a core-sheath conjugate fiber for artificial hair capable of realizing deep colors and having a good appearance close to that of human hair.

BRIEF DESCRIPTION OF THE DRAWINGS

FIG. 1 is a schematic, view showing a fiber cross section of a core-sheath conjugate fiber for artificial hair according to one or more embodiments of the present invention.

DETAILED DESCRIPTION OF THE EMBODIMENTS

The inventors of one or more embodiments of the present invention conducted an in-depth research in order to address the above, and found that, when a core-sheath conjugate fiber for artificial hair is colored, with a color difference between the conjugate fiber and the core part being 3.0 or more and a color difference between the conjugate fiber and the sheath part being also 3.0 or more, the core-sheath conjugate fiber for artificial hair can realize deep colors and obtain colors and appearances close to those of human hair, and thus one or more embodiments of the present invention were achieved.

Color Difference

The color difference is an indicator of a difference between colors of two objects, and the CIE1976 ($L^*$, $a^*$, $b^*$) color space is used for the color difference $\Delta E^*$ in one or more embodiments of the present invention. The CIE1976 ($L^*$, $a^*$, $b^*$) color space is widely used in industrial fields as a color space that is uniform for human's perception, and the color difference $\Delta E^*$ is calculated using Equation (1) based on respective color coordinates of two measurement targets (e.g., 1 and 2) that are to be compared with each other as measured by an ordinary color-difference meter. Note that $L^*$ means lightness, and $a^*$ (with positive values toward red and negative values toward green) and $b^*$ (with positive values toward yellow and negative values toward blue) mean chromaticity, where $L^*1$, $a^*1$, and $b^*1$ are for the measurement target 1, and $L^*2$, $a^*2$, and $b^*2$ are for the measurement target 2.

$$\Delta E^* = [(L^*1 - L^*2)^2 + (a^*1 - a^*2)^2 + (b^*1 - b^*2)^2]^{1/2} \qquad (1)$$

It seems that, since human hair has a complex structure comprised by a plurality of layers such as the cuticle, the cortex, and the medulla, light reflected thereby provides various colors, and a deep and complex appearance unique to human hair is expressed. On the other hand, in an ordinary core-sheath conjugate fiber for artificial hair, the core part and the sheath part have the same color in order to simplify the production processes, and thus its appearance becomes monochromatic and monotonous.

Thus, in a core-sheath conjugate fiber for artificial hair (hereinafter, alternatively referred to simply as a "core-sheath conjugate fiber") according to one or more embodiments of the present invention, the colors of the core part and the sheath part are made significantly different from each other, for example, by combining black and yellow or by combining khaki and beige, and thus it is possible to obtain a deep and complex appearance close to that of human hair. Specifically, in a core-sheath conjugate fiber for artificial hair according to one or more embodiments of the present invention, if the color difference ΔE* between the core-sheath conjugate fiber and the core part is 3.0 or more and the color difference ΔE* between the core-sheath conjugate fiber and the sheath part is also 3.0 or more, it is possible to obtain a good appearance. This state means that a core-sheath conjugate fiber having a core-sheath structure has a color different from the colors of both of the core part and the sheath part constituting the core-sheath conjugate fiber, and a deep and complex appearance resulting from the above-described core-sheath structure is expressed. Both of the color differences ΔE* between the core-sheath conjugate fiber and the core part and between the core-sheath conjugate fiber and the sheath part may be 10 or more. A state in which the color difference ΔE* between the core-sheath conjugate fiber and either the core part or the sheath part is less than 3.0 means that there is no significant difference between the color of the core-sheath conjugate fiber and the color of either the core part or the sheath part, and a deep and complex appearance close to that of human hair cannot be obtained.

Furthermore, if the L* value of the sheath part is larger than the U value of the core part and the difference therebetween is 30 or more, it is possible to obtain an extremely deep appearance. If the L* value of the sheath part is larger than the L* value of the core part, when light passed through the sheath part and reflected off the core part surface again passes through the sheath part and appears on the outer surface, the light appears on the outer surface without being attenuated by the sheath part, and thus not only the light reflected off the sheath part surface but also the light reflected off the core part surface affects color tones, which makes it easy to realize deep colors. Moreover, if the difference between the L* value of the core part and the L* value of the sheath part is 30 or more, when light passed through the sheath part and reflected off the core part surface again passes through the sheath part and appears on the outer surface, the light appears on the outer surface without being attenuated by the sheath part, and thus not only the light reflected off the sheath part surface but also the light reflected off the core part surface affects color tones, which makes it easy to realize deep colors.

Coloring Method

In one or more embodiments of the present invention, the method for coloring the core part or the sheath part is not particularly limited, and coloring may be performed through spun-dyeing or dyeing.

In the present disclosure, the spun-dyeing means coloring performed by adding a pigment to a resin composition that is to be used as a raw material, and, for example, it is possible to obtain a core-sheath conjugate fiber for artificial hair with a desired color, by adding an ordinary pigment such as carbon black or anthraquinone-based pigment to the resin composition. Furthermore, it is also possible to use a pigment masterbatch instead of using a pigment. The pigment masterbatch is obtained by kneading and pelletizing (which may be referred to as "compounding") a pigment and a resin composition using a kneader such as an extruder, wherein a pigment that is typically difficult to handle due to its fine powder form is dispersed in advance in a resin composition, and thus it is possible to easily handle the pigment and to suppress color spots of the obtained fiber.

Furthermore, in a fiber for hair that is required to have a large number of colors, from the viewpoint of simplifying the production and reducing the pigment inventory cost, it is preferable to obtain a fiber spun-dyed to have a desired color, by adding several specific types of pigment masterbatches while adjusting the adding ratio, and, in particular, it is possible to obtain a fiber with a desired color, by adding three types of pigment masterbatches of black, red, and yellow while adjusting the blending ratio thereof. For example, if a 20-wt % pigment masterbatch prepared by blending black:red:yellow=10:60:30 (parts by weight) is added in an amount of 2.0 parts by weight to 100 parts by weight of base resin, it is possible to obtain a conjugate fiber for brown artificial hair.

In the present disclosure, the dyeing means obtaining a colored fiber by causing a dye to be bonded to and absorbed by a fiber after shaping, and, for example, it is possible to use a dispersed dye; an acidic dye, a basic dye, or the like according to the fiber material.

The spun-dyeing and the dyeing may be performed in combination, and it, is possible to use a coloring method suitable for the resin characteristics of the core and the sheath, such as dyeing a fiber that has been spun-dyed in advance, or spun-dyeing a core and dyeing a sheath.

Shape of Core-Sheath Conjugate Fiber

The cross sectional shapes of the core-sheath conjugate fiber for artificial hair and the core part are not particularly limited, and may be, for example, at least one type of shape selected from the group consisting of an elliptical shape, a crossing circle shape, a cocoon shape, a Dharma doll shape, a dog-bone shape, and a ribbon shape. Furthermore, from the viewpoint of esthetic characteristics such as gloss, texture, combing property, and curl-holding properties, the fiber and the core part may have the same flat multilobed cross sectional shape in which the major axis direction of the fiber cross section and the major axis direction of core part cross section substantially match each other. If the fiber and the core part have the same flat multilobed cross sectional shape in which the major axis direction of the fiber cross section and the major axis direction of the core part cross section substantially match each other, in the fiber cross section, the outer circumferential shape of the fiber cross section and the outer circumferential shape of the core part are similar to each other, and thus the thickness of the sheath is uniform, and it is possible to prevent the core part from being exposed to the surface, while maintaining a good touch and appearance as artificial hair. Furthermore, since the fiber and the core part have a flat multilobed cross sectional shape, recesses and projections are formed on the core-sheath interface, which disperses stress that is generated at the core-sheath interface due to deformation such as bending, and thus it is possible to prevent fiber separation due to coming off of the two components from each other. Furthermore, since the major axis directions of the fiber cross section and the core part cross section substantially match each other; the entire fiber and the core part have the same anisotropy of the modulus of elasticity in bending resulting from the moment of inertia of area, and thus it is easy to adjust the quality required for artificial hair, such as a touch and combing property.

FIG. 1 is a schematic view showing a fiber cross section of a core-sheath conjugate fiber for artificial hair according to one or more embodiments of the present invention. A core-sheath conjugate fiber 1 for artificial hair according to this embodiment is comprised by a core part 10 and a sheath part 20, the major axis direction of the fiber cross section and major axis direction of the core part cross section match each other, both of the cross sectional shape of the core-sheath conjugate fiber 1 for artificial hair and the cross sectional shape of the core part 10 are circular, and the core part 10 is arranged concentrically to the core-sheath conjugate fiber 1 for artificial hair.

The above-described cross sectional shapes of the fiber and the core part can be controlled by using nozzle pores with a shape close to the target cross sectional shape.

The ratio (core-to-sheath area ratio) between the core part and the sheath part in the core-sheath conjugate fiber for artificial hair is not particularly limited, but the core-to-sheath area ratio therebetween may be in the range of 1:9 to 9:1, 2:8 to 8:2, or 3:7 to 7:3, from the viewpoint of expression of a complex appearance, spinning processes, and stability of the cross section, for example.

From the viewpoint of suitability for artificial hair, the core-sheath conjugate fiber for artificial hair may have a fiber fineness of 10 dtex or more and 150 dtex or less, 30 dtex or more and 120 dtex or less, 40 dtex or more and 100 dtex or less, or 50 dtex or more and 90 dtex or less.

Fiber Composition

The composition of the core-sheath conjugate fiber for artificial hair is not particularly limited, and may be, for example, such that the core-sheath conjugate fiber for artificial hair is comprised by a thermoplastic resin composition such as an acrylonitrile-based resin composition, a vinyl chloride-based resin composition, a vinylidene chloride-based resin composition, a polyester-based resin composition, a polyamide-based resin composition, or a polyolefin-based resin composition. Furthermore, these resin compositions may be used in a combination of two or more. Furthermore, from the viewpoint of flame retardancy a flame retardant may be used in combination, and a polyester-based resin composition containing a polyester-based resin and a bromine-based polymer flame retardant, a polyamide-based resin composition containing a polyamide-based resin and a bromine-based polymer flame retardant, and the like may be used, wherein examples of the flame-retardant resin composition include a resin composition containing 100 parts by weight of one or more types of resins selected from the group consisting of polyalkylene terephthalate, a copolymerized polyester mainly containing polyalkylene terephthalate, and polyamide, and 5 parts by weight or more and 40 parts by weight or less of bromine-based polymer flame retardant.

Of these compositions, it is preferable to use a polyester-based resin composition or a polyamide resin composition, from the viewpoint of satisfactory heat resistance and fiber physical properties required for a fiber for artificial hair and relatively good handleability in production processes such as resin treatment, spinning, drawing, and heat treatment, and it is more preferable to use a flame-retardant resin composition for one or both of the core part and the sheath part from the viewpoint of safety.

The polyalkylene terephthalate is not particularly limited, and may be, for example, polyethylene terephthalate, polypropylene terephthalate, polybutylene terephthalate, or polycyclohexane dimethylene terephthalate. The copolymerized polyester mainly containing polyalkylene terephthalate is not particularly limited, and may be, for example, a copolymerized polyester mainly containing polyalkylene terephthalate such as polyethylene terephthalate, polypropylene terephthalate, polybutylene terephthalate, or polycyclohexane dimethylene terephthalate, and further containing other copolymerizable components. In the present disclosure, the "copolymerized polyester mainly containing polyalkylene terephthalate" refers to a copolymerized polyester containing polyalkylene terephthalate in an amount of 80 mol % or more.

Examples of the other copolymerizable components include; polycarboxylic acids such as isophthalic acid, orthophthalic acid, naphthalenedicarboxylic acid, paraphenylenedicarboxylic acid, trimellitic acid, pyromellitic acid, succinic acid, glutamic acid, adipic acid, suberic acid, azelaic acid, sebacic acid, and dodecanedioic acid, and their derivatives; dicarboxylic acids and their derivatives containing sulfonates such as 5-sodiumsulfoisophthalic acid and dihydroxyethyl 5-sodiumsilfoisophthalate; 1,2-propanediol; 1,3-propanediol; 1,4-butanediol; 1,6-hexanediol; neopentyl glycol; 1,4-cydohexanedimethanol; diethylene glycol; polyethylene glycol; trimethylolpropane; pentaerythritol; 4-hydroxybenzoic acid; ε-caprolactone; and an ethylene glycol ether of bisphenol A.

The copolymerized polyester may be produced by adding a small amount of other copolymerizable components to polyalkylene terephthalate serving as a main component, and allowing them to react with each other, from the viewpoint of stability and ease of operation. Examples of the polyalkylene terephthalate include a polymer of terephthalic acid and/or its derivatives (e.g., methyl terephthalate) and alkylene glycol. The copolymerized polyester may be produced by adding a small amount of monomer or oligomer component serving as other copolymerizable components, to a mixture of terephthalic acid and/or its derivatives (e.g., methyl terephthalate) and alkylene glycol, used for polymerization of polyalkylene terephthalate serving as a main component, and subjecting them to polymerization.

It is sufficient that the copolymerized polyester has a structure in which the other copolymerizable components are polycondensed on the main chain and/or side chain of polyalkylene terephthalate serving as a main component, and the copolymerization method and the like are not particularly limited.

Specific examples of the copolymerized polyester mainly containing polyalkylene terephthalate include a polyester obtained through copolymerization of polyethylene terephthalate serving as a main component with one compound selected from the group consisting of an ethylene glycol ether of bisphenol A, 1,4-cydohexanedimethanol, isophthalic acid, and dihydroxyethyl 5-sodiumsulfoisophthalate.

The polyalkylene terephthalate and the copolymerized polyester mainly containing polyalkylene terephthalate may be used alone or in a combination of two or more. In particular, polyethylene terephthalate (hereinafter, alternatively referred to as "PET"); polypropylene terephthalate; polybutylene terephthalate; a polyester obtained through copolymerization of polyethylene terephthalate serving as a main component with an ethylene glycol ether of bisphenol A; a polyester obtained through copolymerization of polyethylene terephthalate serving as a main component with 1,4-cyclohexanedimethanol; a polyester obtained through copolymerization of polyethylene terephthalate serving as a main component with isophthalic acid; a polyester obtained through copolymerization of polyethylene terephthalate serving as a main component with dihydroxyethyl 5-sodiumsulfoisoplithalate, and the like may be used alone or in a combination of two or more.

The polyamide-based resin means a nylon resin obtained through polymerization of one or more selected from the group consisting of lactam, aminocarboxylic acid, a mixture of dicarboxylic acid and diamine, a mixture of a dicarboxylic acid derivative and diamine, and a salt of dicarboxylic acid and diamine.

Specific examples of the lactam include, but are not particularly limited to, for example, 2-azetidinone, 2-pyrrolidinone, 5-valerolactam, ε-caprolactam, enantholactam, capryllactam, undecalactam, and laurolactani. Of these lactams, it is preferable to use ε-caprolactam, undecalactam, and laurolactam, and more preferable to use ε-caprolactam. These lactams may be used alone or in a combination of two or more.

Specific examples of the aminocarboxylic acid include, but are not particularly limited to, for example, 6-aminocaproic acid, 7-aminoheptanoic acid, 8-aminooctanoic acid, 9-aminononanoic acid, 10-aminodecanoic acid, 11-aminoundecanoic acid, and 12-aminododecanoic acid. Of these aminocarboxylic acids, it is preferable to use 6-aminocaproic acid, 11-aminoundecanoic acid, and 12-aminododecanoic acid, and more preferable to use 6-aminocaproic acid. These aminocarboxylic acids may be used alone or in a combination of two or more.

Specific examples of the dicarboxylic acid that can be used for the mixture of dicarboxylic acid and (hairline, the mixture of a dicarboxylic acid derivative and diamine, or the salt of dicarboxylic acid and diamine include, but are not particularly limited to, for example: aliphatic dicarboxylic acids such as oxalic acid, malonic acid, succinic acid, glutaric acid, adipic acid, pimelic acid, suberic acid, azelaic acid, sebacic acid, undecanedioic acid, dodecanedioic acid, brasylic acid, tetradecanedioic acid, pentadecanedioic acid, and octadecanedioic acid; alicyclic dicarboxylic acids such as cyclohexane dicarboxylic acid; and aromatic dicarboxylic acids such as phthalic acid, isophthalic acid, terephthalic acid, and naphthalenedicarboxylic acid. Of these dicarboxylic acids, it is preferable to use adipic acid, sebacic acid, dodecanedioic acid, terephthalic acid, and isophthalic acid, and more preferable to use adipic acid, terephthalic acid, and isophthalic acid. These dicarboxylic acids may be used alone or in a combination of two or more.

Specific examples of the diamine that can be used for the mixture of dicarboxylic acid and diamine, the mixture of a dicarboxylic acid derivative and diamine, or the salt of dicarboxylic acid and diamine include, but are not particularly limited to, for example: aliphatic diamines such as 1,4-diaminobutane, 1,5-diaminopentane, 1,6-diaminohexane, 2-methyl-1,5-diaminopentane (MDP), 1,7-diaminoheptane, 1,8-diaminooctane, 1,9-diaminononan, 1,10-diaminodecane, 1,11-diaminoundecane, 1,12-diaminododecane, 1,13-diaminotridecane, 1,14-diaminotetradecane, 1,15-diaminopentadecane, 1,16-diaminohexadecane, 1,17-diaminoheptadecane, 1,18-diaminooctadecane, 1,19-diaminononadecane, and 1,20-diaminoeicosane; alicyclic diamines such as cyclohexanediamine and bis-(4-aminohexyl)methane; and aromatic diamines such as m-xylylenediamine and p-xylylenediamine. Of these diamines, it is preferable to use an aliphatic diamine, and more preferable to use hexamethylenediamine. These diamines may be used alone or in a combination of two or more.

The polyamide-based resin is not particularly limited, but it is preferable to use, for example, Nylon 6, Nylon 66 (hereinafter, alternatively referred to as "PA66"), Nylon 11, Nylon 12, Nylon 6/10, Nylon 6/12, semi-aromatic nylon containing the Nylon 6T and/or 6I unit, copolymers of these nylon resins, or the like. It is more preferable to use Nylon 6, Nylon 66, or a copolymer of Nylon 6 and Nylon 66.

The polyimide-based resin can be produced for example, using a polyamide-based resin polymerization method in which a polyamide-based resin raw material is heated in the presence or absence of a catalyst. During the polymerization, stirring may or may not be performed, but it is preferable to perform stirring in order to obtain a uniform product. The polymerization temperature can be set as appropriate according to the degree of polymerization, the reaction yield, and the reaction time of a target polymer, but it is preferable to set the temperature to a low temperature in consideration of the quality of a finally obtained polyamide-based resin. The reaction ratio can also be set as appropriate. The pressure is not limited, but it is preferable to reduce the pressure in the system in order to efficiently let volatile components move to the outside of the system.

The polyamide-based resin for use in one or more embodiments of the present invention may have a terminal end that is capped by an end-capping agent such as a carboxylic acid compound or an amine compound as necessary. The concentration of terminal end amino groups or terminal end carboxyl groups in a nylon resin obtained when a terminal end is capped by adding monocarboxylic acid or monoamine is lower than that when such an end-capping agent is not used. On the other hand, the total concentration of terminal end amino groups and terminal end carboxyl groups does not change when a terminal end is capped by dicarboxylic acid or diamine, but the concentration ratio between terminal end amino groups and terminal end carboxyl groups changes.

Specific examples of the carboxylic acid compound include, but are not particularly limited to, for example: aliphatic monocarboxylic acids such as acetic acid, propionic acid, butyric acid, valeric acid, caproic acid, enanthic acid, caprylic add, pelargonic acid, undecanoic acid, lauric acid, tridecanoic acid, myristic acid, myristoleic acid, palmitic acid, stearic acid, oleic acid, linoleic acid, and arachic acid; alicyclic monocarboxylic acids such as cyclohexanecarboxylic acid and methylcyclohexanecarboxylic acid; aromatic monocarboxylic acids such as benzoic acid, toluic acid, ethylbenzoic acid, and phenylacetic acid; aliphatic dicarboxylic acids such as oxalic acid, malonic acid, succinic acid, glutaric acid, adipic acid, pimelic acid, suberic acid, azelaic acid, sebacic acid, undecanedioic acid, dodecanedioic acid, brasylic acid, tetradecanalioic acid, pentadecanedioic acid, and octadecanedioic acid; alicyclic dicarboxylic acids such as cydohexanedicarboxylic acid; and aromatic dicarboxylic acids such as phthalic acid, isophthalic acid, terephthalic acid, and naphthalenedicarboxylic acid.

Specific examples of the amine compound include, but are not particularly limited to, for example: aliphatic monoamines such as butylamine, pentylamine, hexylamine, heptylamine, octylamine, 2-ethylhexylamine, nonylamine, decylamine, undecylamine, dodecylamine, tridecylamine, tetradecylamine, pentadecylamine, hexadecylamine, octadecylamine, nonadecylamine, and icosylamine; alicyclic monoamines such as cydohexylamine and methylcyclohexylamine; aromatic monoamines such as benzylamine and β-phenylethylamine; aliphatic diamines such as 1,4-diaminobutane, 1,5-diaminopentane, 1,6-diaminohexane, 1,7-diaminoheptane, 1,8-diaminooctane, 1,9-diaminononan, 1,10-diaminodecane, 1,11-diaminoundecane, 1,12-diaminododecane, 1,13-diaminotridecane, 1,14-diaminotetradecane, 1,15-diamino pentadecane, 1,16-diamnohexadecane, 1,17-diaminoheptadecane, 1,18-diaminooctadecane, 1,19-diaminononadecane, and 1,20-diaminoeicosane; alicyclic diamines such as cyclohexanediamine and bis-(4-aminohexyl)methane; and aromatic diamines such as xylylenediamine.

The terminal end group concentration of the polyimide-based resin is not particularly limited, but the terminal end amino group concentration nay be high, for example, when it is necessary to increase the dyeability for fiber uses or when designing a material suitable for alloying for resin uses. On the other hand, the terminal end amino group concentration may be low, for example, when it is required to suppress coloring or gelation under extended aging conditions. Furthermore, the terminal end carboxyl group concentration and the terminal end amino group concentration may be both low when it is required to suppress reproduction of lactam during re-melting, yarn breakage during melt spinning due to production of oligomer, mold deposit during continuous injection molding, and generation of die marks during continuous extrusion of a film. It is preferable to adjust the terminal end group concentration according to the applications, but the terminal end amino group concentration and the terminal end carboxyl group concentration may be both $1.0 \times 0^{-5}$ to $15.0 \times 10^{-5}$ eq/g, $2.0 \times 10^{-5}$ to $12.0 \times 10^{-5}$ eq/g, or $3.0 \times 10^{-5}$ to $11.0 \times 10^{-5}$ eq/g.

The intrinsic viscosity (alternatively referred to as an "IV value") of each of the polyester resin and the polyimide resin is not particularly limited, but it may be 0.3 or more and 1.2 or less, or 0.4 or more and 1.0 or less. If the intrinsic viscosity is 0.3 or more, the mechanical strength of the obtained fiber does not decrease, and there is no risk of dripping during a combustion test. On the other hand, if the intrinsic viscosity is 1.2 or less, the molecular weight is not like other than an epoxy group or tribromophenol, or may be bound to a polyester component through an ester group.

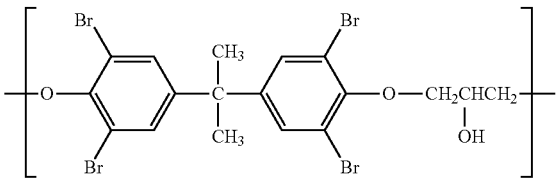

(1)

Furthermore, part of the structure of the brominated epoxy-based flame retardant, other than the molecular end, may be changed. For example, the brominated epoxy-based flame retardant may have a branched structure in which the secondary hydroxyl group and the epoxy group are bound. Also, part of the bromine of the chemical formula (1) above may be eliminated or added, as long as the bromine content in the molecules of the brominated epoxy-based flame retardant does not change significantly.

For example, a polymeric brominated epoxy-based flame retardant as represented by the chemical formula (2) below may be used as the brominated epoxy-based flame retardant. In the chemical formula (2) below, in is 1 to 1000. Examples of the polymeric brominated epoxy-based flame retardant represented by the chemical formula (2) below include a commercially available product such as a brominated epoxy-based flame retardant (product name "SR-T2MP") manufactured by Sakamoto Yakuhin Kogyo Co., Ltd.

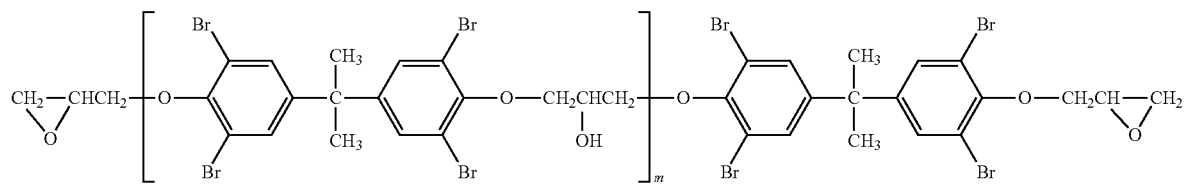

(2)

too large, and the melt viscosity is not too high, and thus it is easy to perform melt spinning, and the fineness is likely to be uniform.

The bromine-based polymer flame retardant is not particularly limited, but, for example, it is preferable to use a brominated epoxy-based flame retardant from the viewpoint of heat resistance and flame retardancy. The brominated epoxy-based flame retardant may use, as a raw material, a brominated epoxy-based flame retardant having an epoxy group or tribromophenol at a molecular end thereof. The structure of the brominated epoxy-based flame retardant after melt kneading is not particularly limited, but it is preferable that 80 mol % or more of the structure is comprised by a constituent unit represented by the chemical formula (1) below when the total number of constituent units each represented by the chemical formula (1) below and constituent units obtained by at least partially modifying the chemical formula (1) below is taken as 100 mol %. The structure of the brominated epoxy-based flame retardant may change at a molecular end thereof after melt kneading. For example, a molecular end of the brominated epoxy-based flame retardant may be substituted by a hydroxyl group, a phosphate group, a phosphonic acid group, or the From the viewpoint of obtaining a touch and appearance closer to those of human hair and improving the curling properties and curl-holding properties, the core part of the core-sheath conjugate fiber for artificial hair may be comprised by a polyester-based resin composition containing, as a main component resin, one or more types of polyester resins selected from the group consisting of poly alkylene terephthalate and a copolymerized polyester mainly containing polyalkylene terephthalate, and the sheath part thereof may be comprised by a polyamide-based resin composition containing, as a main component resin, a polyamide-based resin mainly containing at least one selected from the group consisting of Nylon 6 and Nylon 66. In an embodiment of the present disclosure, the "polyamide-based resin mainly containing at least one selected from the group consisting of Nylon 6 and Nylon 66" means a polyamide-based resin containing Nylon 6 and/or Nylon 66 in an amount of 80 mol % or more.

In the present disclosure, the "main component resin" means a resin with the highest content among resins contained in the resin composition.

The polyester-based resin composition constituting the core part may further contain other resins in addition to the polyester-based resin serving as a main component resin. When the total amount of resins in the polyester-based resin composition is taken as 100% by weight, the polyester-based resin serving as the main component resin may be contained in an amount of more than 50% by weight, 70% by weight or more, 85% by weight or more, 90% by weight or more, 95% by weight or more, or 100% by weight. Examples of the other resins include a polyamide-based resin, a vinyl chloride-based resin, a modacrylic-based resin, a polycarbonate-based resin, a polyolefin-based resin, and a polyphenylenesulfide-based resin. These resins may be used alone or in a combination of two or more.

The polyamide-based resin composition constituting the sheath part may further contain other resins in addition to the polyamide-based resin serving as a main component resin. When the total amount of resins in the polyamide-based resin composition is taken as 100% by weight, the polyamide-based resin serving as the main component resin may be contained in an amount of more than 50% by weight, 70% by weight or more, 85% by weight or more, 90% by weight or more, 95% by weight or more, or 100% by weight. Examples of the other resins include a polyester-based resin, a vinyl chloride-based resin, a modacrylic-based resin, a polycarbonate-based resin, a polyolefin-based resin, and a polyphenylenesulfide-based resin. These resins may be used alone or in a combination of two or more.

As necessary the core-sheath conjugate fiber for artificial hair of one or more embodiments of the present invention may contain various types of additives such as a flame retardant other than a brominated epoxy-based flame retardant, an auxiliary flame retardant, a heat-resistant agent, a stabilizer, a fluoresces, an antioxidant, an antistatic agent, and a lubricant.

Examples of the flame retardant other than a brominated epoxy-based flame retardant include a phosphorus-containing flame retardant and a bromine-containing flame retardant. Examples of the phosphorus-containing flame retardant include a phosphoric acid ester amide compound and an organic cyclic phosphorus-based compound. Examples of the bromine-containing flame retardant include: bromine-containing phosphoric acid esters such as pentabromotoluene, hexabromobenzene, decabromodiphenyl, decabromodiphenyl ether, bis(tribromophenoxy)ethane, tetrabromophthalic anhydride, ethylene bis(tetrabromophthalimide), ethylene bis(pentabromophenyl), octabromotrimethylphenylindan, and tris(tribromoneopentyl)phosphate; brominated polystyrenes; brominated polybenzyl acrylates; a brominated phenoxy resin; brominated polycarbonate oligomers; tetrabromobisphenol A and tetrabromobisphenol A derivatives such as tetrabromobisphenol A-bis (2,3-dibromopropyl ether), tetrabromobisphenol A-bis (allylether), and tetrabromobisphenol A-bis(hydroxyethyl ether); bromine-containing triazine compounds such as tris (tribromophenoxy)triazine; and bromine-containing isocyanuric acid compounds such as tris(2,3-dibromopropyl)isocyanurate. Of these compounds, it is preferable to use one or more selected from the group consisting of a phosphoric acid ester amide compound, an organic cyclic phosphorus-based compound, and a brominated phenoxy resin flame retardant, from the viewpoint of excellent flame retardancy.

Examples of the auxiliary flame retardant include an antimony-based compound and a composite metal including antimony Examples of the antimony-based compound include antimony trioxide, antimony tetraoxide, antimony pentoxide, sodium antimonate, potassium antimonate, and calcium antimonate. It is more preferable to use one or more selected from the group consisting of antimony trioxide, antimony pentoxide, and sodium antimonate, from the viewpoint of improving the flame retardancy and the influence on a touch.

Examples of the lubricant may include a montanic acid-based wax, a montanic acid ester-based wax, a partially saponified montanic acid-based wax, a montanic acid metal salt, a polyethylene-based wax, a polyethylene oxide-based wax, a polytetrafluoroethylene, a fluorine-based wax, a polydimethyl silicone, and a modified silicone resin, because their influence on fiber physical properties of an antimony compound such as dispersibility, flame retardancy, and heat resistance is small. These compounds may be used alone or in a combination of two or more.

It is possible to form appropriate projections and recesses on the surface of a core-sheath conjugate fiber for artificial hair according to one or more embodiments of the present invention, by performing treatment with chemicals or adding fine particles, from the viewpoint of adjusting gloss and texture. Examples of the fine particles include composite particles mainly containing calcium carbonate, silicon oxide, titanium oxide, aluminum oxide, zinc oxide, talc, kaolin, montmorillonite, bentonite, mica, and silicon oxide. These fine particles may be used alone or in a combination of two or more.

Production Method

It is preferable to use the melt spinning method of one or more embodiments of the present invention, and, for example, in the case of a polyester-based resin composition, melt spinning is performed while the temperatures of an extruder, a gear pump, a nozzle, and the like are set to 250° C. or more and 300° C. or less, after which the obtained spun yarns are allowed to pass through a heated tube, cooled to a temperature of not more than the glass transition point of polyester resin, and wound up at a speed of 50 m/min or more and 5000 in/min or less, and thus spun yarns (undrawn yarns) are obtained. Furthermore, in the case of a polyamide-based resin composition, melt spinning is performed while the temperatures of an extruder, a gear pump, a nozzle, and the like are set to 260° C. or more and 320° C. or less, after which the obtained spun yarns are allowed to pass through a heated tube, cooled to a temperature of not more than the glass transition point of polyamide resin, and wound up at a speed of 50 m/min or more and 5000 nil/min or less, and thus spun yarns (undrawn yarns) are obtained. During the melt spinning, it is possible to supply a thermoplastic resin composition for constituting the core part from a extruder for core, supply a thermoplastic resin composition for constituting the sheath part from a extruder for sheath, and extrude molten polymer through a core-sheath conjugate spinning nozzle (pores) with a predetermined shape.

If the core-sheath conjugate fiber for artificial hair is comprised by a thermoplastic resin composition such as a polyester-based resin composition, it is possible to produce a core-sheath conjugate fiber for artificial hair by melt kneading the thermoplastic resin composition through melt kneading using various types of ordinary kneaders, pelletizing the polyester resin composition after melt kneading, and then performing melt spinning using a core-sheath conjugate spinning nozzle. Moreover the spun yarns may also be cooled in a water bath containing cooling water so as to control the fineness. The temperature and length of the heated tube, the temperature and amount of the cooling air applied, the temperature of the cooling water bath, the cooling time, and the winding speed can be adjusted appropriately in accordance with the extrusion rate of the polymer and the number of holes of the nozzle.

It is preferable that the spun yarns (undrawn yarns) are hot drawn. The drawing may be performed by either a two-step method or a direct drawing method. In the two-step method, the spun yarns are wound once, and then drawn. In the direct drawing method, the spun yarns are drawn continuously without winding. The hot drawing may be performed by a single-stage drawing method or a multi-stage drawing method that includes two or more stages.

The heating means for the hot drawing may be a heating roller, a heat plate, a steam jet apparatus, or a hot water bath, which can be used in combination as desired.

It is also possible to make the touch and texture closer to those of human hair, by adding an oil such as a fiber treatment agent and a softener to the core-sheath conjugate fiber for artificial hair. Examples of the fiber treatment agent include a silicone-based fiber treatment agent and a non-silicone-based fiber treatment agent for improving the touch and the combing property.

The fiber for artificial hair may be subjected to treatment through gear crimping. Accordingly, it is possible to make a fiber gently curved and have a natural appearance, and to reduce the contact between fibers, thereby improving the combing property. In this treatment through gear crimping, typically, a fiber heated to the softening temperature or more is caused to pass through a portion between two meshing gears, so that the shape of the gears is transferred to the fiber and the fiber is thus curved. Furthermore, as necessary, it is also possible to make a fiber curled in different shapes by thermally treating the core-sheath conjugate fiber for artificial hair at different temperatures during the fiber treatment processes.

Hair Ornament Product

The core-sheath conjugate fiber for artificial hair can be used for hair ornament products without particular limitation. For example, it is possible to use the core-sheath conjugate fiber for hair wigs, hairpieces, weaving hair, hair extensions, braided hair, hair accessories, doll hair, and the like.

The hair ornament product may be constituted only by the core-sheath conjugate fiber for artificial hair of one or more embodiments of the present invention, or by the core-sheath conjugate fiber for artificial hair of one or more embodiments of the present invention combined with other fibers for artificial hair and natural fibers such as human hair and animal hair.

EXAMPLES

Hereinafter, one or more embodiments of the present invention will be more specifically described by way of examples. Note that one or more embodiments of the present invention are not limited to these examples.

The measuring methods and the evaluation methods used in the examples and comparative examples are as follows.

Single Fiber Fineness

The measurement was performed using an autovibro type fineness measuring apparatus "Denier Computer type DC-11" (manufactured by Search), and an average of measured values of 30 samples was calculated and taken as the single fiber fineness.

Color Measurement

Fibers were bundled at room temperature and fixed with a shrinkage tube such that the fiber bundle was not displaced, and thus a fiber bundle for color measurement was prepared. This fiber bundle was subjected to measurement using a color measurement apparatus ("MAMBO" manufactured by Fossa. Nova Technologies), and thus $L^*a^*b^*$ data was acquired.

Furthermore, the color of each of the core part and the sheath part was acquired by observing the cross section using a digital microscope (VHX-6000 manufactured by Keyence Corporation) and converting the color information into numerals to obtain the RGB value of the core part or the sheath part, and calculating $L^*a^*b^*$ from the value.

The color difference $\Delta E^*$ between the fiber and the core part and the color difference $\Delta E^*$ between the fiber and the sheath part were calculated using the equation (1) below. The $L^*1$, $a^*1$, and $b^*1$ are for a measurement target 1, and $L^*2$, $a^*2$, and $b^*2$ are for a measurement target 2.

$$\Delta E^* = [(L^*1 - L^*2)^2 + (a^*1 - a^*2)^2 + (b^*1 - b^*2)^2]^{1/2} \quad (1)$$

Appearance Evaluation

The appearances of the examples and comparative examples were subjected to sensory evaluation by professional hairstylists in four stages below A: Similar appearance to that of human hair (extremely good with deep colors and deep appearance)
B: Substantially similar appearance to that of human hair (very good with deep colors and deep appearance)
C: Slightly poor appearance compared with that of human hair (good with deep colors and deep appearance)
D: Bad appearance that is poor compared with that of human hair Example 1

First, 20 parts by weight of brominated epoxy-based flame retardant (product name "SR-T2MP" manufactured by Sakamoto Yakuhin Kogyo Co., Ltd.), 2 parts by weight of sodium antimonate (product name "SA-A" manufactured by Nihon Seiko Co., Ltd.), 0.2 parts by weight of montanic acid-based wax/fluorine-based wax blended product (wax composite, product name "G431L" manufactured by Clariant Japan), 2 parts by weight of black pigment masterbatch (product name "PESM22367BLACK (20)" manufactured by Dainichiseika. Color & Chemicals Mfg. Co., Ltd., pigment: 20% by weight, base resin: polyester-based resin), 0.7 parts by weight of yellow pigment masterbatch (product name "PESM1001YELLOW (20)" manufactured by Dainichiseika Color & Chemicals Mfg. Co., Ltd., pigment: 20% by weight, base resin: polyester-based resin), and 0.5 parts by weight of red pigment masterbatch (product name "PESM3005RED (20)" manufactured by Dainichiseika Color & Chemicals Mfg. Co., Ltd., pigment: 20% by weight, base resin: polyester-based resin) were added to and dry blended with 100 parts by weight of polyethylene terephthalate (East PET product name "A-12" manufactured by East West Chemical Private Limited) dried to a moisture content of 100 ppm or less, and the mixture was supplied to a twin-screw extruder, melt kneaded at a barrel set temperature of 280° C., and pelletized, after which the pellets were dried to a moisture content of 100 ppm or less, and thus a polyester-based resin composition was obtained.

Subsequently, 1 part by weight of silica/melamine composite particles (product name "Optbeads 2000M" manufactured by Nissan Chemical Corporation), 2 parts by weight of black pigment masterbatch (product name "PESM22367BLACK (1)" manufactured by Dainichiseika Color & Chemicals Mfg. Co., Ltd., pigment: 20% by weight, base resin: polyester-based resin), 1 part by weight of yellow pigment masterbatch (product name "PESM1001YELLOW (20)" manufactured by Dainichiseika Color & Chemicals Mfg. Co., Ltd., pigment: 20% by weight, base resin: polyester-based resin), and 0.7 parts by weight of red pigment masterbatch (product name "PESM3005RED (20)" manufactured by Dainichiseika Color & Chemicals Mfg. Co., Ltd., pigment: 20% by weight, base resin: polyester-based resin) were added to and dry blended with 100 parts by weight of Nylon 66 (product name "Zytel42A" manufactured by DuPont) dried to a moisture content of 1000 ppm or less, and the mixture was supplied to a twin-screw extruder, melt kneaded at a barrel set temperature of 280° C., and pelletized, after which the pellets were dried to a moisture content of 1000 ppm or less, and thus a poly amide-based resin composition was obtained.

Next, the polyester-based resin composition and polyamide-based resin composition in the form of pellets were each supplied to an extruder, extruded from concentric core-sheath conjugate spinning nozzle pores (the number of pores 120, pore diameter 1.5 mm) at a set temperature of 280° C. and wound up at a speed of 40 to 200 m/min, and thus undrawn yarns of core-sheath conjugate fibers each having a core part comprised by the polyester-based resin composition and a sheath part comprised by the polyamide-based resin composition, and having a core-to-sheath area ratio of 7:3 were obtained.

The obtained undrawn yarns were drawn to 3 times while being wound up at a speed of 45 m/min using a heat roll at 85° C., and, continuously after this treatment, the yarns were heat treated by being wound up at a speed of 45 m/min. using a heat roll heated to 200° C. Then, after application of a polyether-based oil (product name "KWC-Q" manufactured by Marubishi Oil Chemical Corporation) in an amount of 0.20% omf (by oil pure weight percentage with respect to the dry fiber weight), the yarns were dried, and thus a core-sheath conjugate fiber (with a single fiber fineness of 62 dtex) having the cross sectional shape shown in FIG. 1 was obtained.

Example 2

A core-sheath conjugate fiber (with a single fiber fineness of 58 dtex) was obtained in a similar way to that of Example 1, except that the core-to-sheath area ratio was changed to 5:5.

Example 3

A core-sheath conjugate fiber (with a single fiber fineness of 62 dtex) was obtained in a similar way to that of Example 1, except that the pigments blended for the polyamide-based resin composition of the sheath were changed to 1 part by weight of black pigment masterbatch (product name "PESM22367BLACK (1)" manufactured by Dainichiseika Color & Chemicals Mfg. Co., Ltd.) and 3 parts by weight of red pigment masterbatch (product name "PESM3005RED (20)" manufactured by Dainichiseika Color & Chemicals Mfg. Co., Ltd.).

Example 4

A core-sheath conjugate fiber (with a single fiber fineness of 55 dtex) was obtained in a similar way to that of Example 3, except that the core-to-sheath area ratio was changed to 3:7.

Example 5

A core-sheath conjugate fiber (with a single fiber fineness of 55 dtex) was obtained in a similar way to that of Example 1, except that the pigments blended for the polyester-based resin composition of the core were changed to 0.1 parts by weight of black pigment masterbatch (product name "PESM22367BLACK (20)" manufactured by Dainichiseika Color & Chemicals Mfg. Co., Ltd.), 0.7 parts by weight of yellow pigment masterbatch (product name "PESM1001YELLOW (20)" manufactured by Dainichiseika Color & Chemicals Mfg. Co., Ltd.), and 0.4 parts by weight of red pigment masterbatch (product name "PESM3005RED (20)" manufactured by Dainichiseika Color & Chemicals Mfg. Co., Ltd.), and that the pigments blended for the polyamide-based resin composition of the sheath were changed to 0.2 parts by weight of black pigment masterbatch (product name "PESM22367BLACK (1)" manufactured by Dainichiseika Color & Chemicals Mfg. Co., Ltd.), 0.1 parts by weight of yellow pigment masterbatch (product name "PESM1.001YELLOW (20)" manufactured by Dainichiseika Color & Chemicals Mfg. Co., Ltd.), and 0.2 parts by weight of red pigment masterbatch (product name "PESM3005RED (1)" manufactured by Dainichiseika Color & Chemicals Mfg. Co., Ltd.).

Example 6

A core-sheath conjugate fiber (With a single fiber fineness of 55 dtex) was obtained in a similar way to that of Example 5, except that the polyamide-based resin composition was used for the core and the polyester-based resin composition was used for the sheath.

Example 7

A core-sheath conjugate fiber (with a single fiber fineness of 62 dtex) was obtained in a similar way to that of Example 5, except that the pigments blended for the polyester-based resin composition of the core were changed to 0.2 parts by weight of black pigment masterbatch (product name "PESM22367BLACK (20)" manufactured by Dainichiseika Color & Chemicals Mfg. Co., Ltd.), 2 parts by weight of yellow pigment masterbatch (product name "PESM1001YELLOW (1)" manufactured by Dainichiseika Color & Chemicals Mfg. Co., Ltd.), and 0.03 parts by weight of blue pigment masterbatch (product name "K-501(30)" manufactured by Dainichiseika Color & Chemicals Mfg. Co., Ltd.).

Example 8

A core-sheath conjugate fiber (with a single fiber fineness of 55 dtex) was obtained in a similar way to that of Example 7, except that the core-to-sheath area ratio was changed to 3:7.

Example 9

A core-sheath conjugate fiber (with a single fiber fineness of 62 dtex) was obtained in a similar way to that of Example 5, except that the pigments blended for the polyester-based resin composition of the core were changed to 2 parts by weight of black pigment masterbatch (product name "PESM22367BLACK (1)" manufactured by Dainichiseika Color & Chemicals Mfg. Co., Ltd.), 0.02 parts by weight of blue pigment masterbatch (product name "K-501 (30)" manufactured by Dainichiseika Color & Chemicals Mfg. Co., Ltd.), and 0.07 parts by weight of purple pigment masterbatch (product name "K-40 (20)" manufactured by Dainichiseika Color & Chemicals Mfg. Co., Ltd.).

Example 10

A core-sheath conjugate fiber (with a single fiber fineness of 62 dtex) was obtained in a similar way to that of Example 7, except that the core-to-sheath area ratio was changed to 3:7.

Comparative Example 1

A core-sheath conjugate fiber (with a single fiber fineness of 58 dtex) was obtained in a similar way to that of Example 1, except that the pigments blended for the polyamide-based resin composition were changed to 2 parts by weight of black pigment masterbatch (product name "PESM22367BLACK (20)" manufactured by Dainichiseika Color & Chemicals Mfg. Co., Ltd.), 0.7 parts by weight of yellow pigment masterbatch (product name "PESM1001YELLOW (20)" manufactured by Dainichiseika Color & Chemicals Mfg. Co., Ltd.), and 0.5 parts by weight of red pigment masterbatch (product name "PESM3005RED (20)" manufactured by Dainichiseika Color & Chemicals Mfg. Co., Ltd.).

Tables 1 and 2 below show the results of measurement of the color differences ΔE* and evaluation of the appearances performed as described above on the fibers obtained in Examples 1 to 10 and Comparative Example 1.

TABLE 1

|  |  | Ex. 1 | Ex. 2 | Ex. 3 | Ex. 4 | Ex. 5 | Ex. 6 |
|---|---|---|---|---|---|---|---|
| Core resin/Color |  | PET/Black | PET/Black | PET/Black | PET/Black | PET/Light brown | PA66/Beige |
| Sheath resin/Color |  | PA66rfellow | PA66/Yel low | PA66/Red | PA66/Red. | PA66/Beige | PET/Light brown |
| Core-to-sheath area ratio |  | 7:3 | 5:5 | 7:3 | 3:7 | 7:3 | 7:3 |
| Color coordinates of core-sheath conjugate fiber | $L^*$ | 20.82 | 25.66 | 19.86 | 23.57 | 44.89 | 55.33 |
|  | $a^*$ | 2.15 | 7.94 | 5.71 | 19.03 | 11.76 | 11.82 |
|  | $b^*$ | 1.63 | 6.38 | 0.97 | 1.91 | 18.24 | 20.6 |
| Color coordinates of core alone | $L^*$ | 18.03 | 18.03 | 18.03 | 18.03 | 39.78 | 69.27 |
|  | $a^*$ | −0.99 | −0.99 | −0.99 | −0.99 | 3.40 | −6.78 |
|  | $b^*$ | 1.94 | 1.94 | 1.94 | 1.94 | 17.67 | 18.72 |
| $\Delta E^*$ from core |  | 4.21 | 12.56 | 7.01 | 20.77 | 9.81 | 23.32 |
| Color coordinates of sheath alone | $L^*$ | 51.71 | 51.71 | 31.15 | 31.15 | 69.27 | 39.78 |
|  | $a^*$ | −0.03 | −0.03 | 30.58 | 30.58 | −6.78 | 3.4 |
|  | $b^*$ | 27.61 | 27.61 | 10.05 | 10.05 | 18.72 | 17.67 |
| $\Delta E^*$ from sheath |  | 40.42 | 34.54 | 28.78 | 16.03 | 30.63 | 17.92 |
| Core-sheath L difference |  | 33.68 | 33.68 | 13.12 | 13.12 | 29.49 | −29.49 |
| Appearance evaluation |  | C | A | C | B | C | B |

TABLE 2

|  |  | Ex. 7 | Ex. 8 | Ex. 9 | Ex. 10 | Com.Ex.1 |
|---|---|---|---|---|---|---|
| Core resin/Color |  | PET/Khaki | PET/Khaki | PET/Light blue | PA66/Light blue | PET/Black |
| Sheath resin/Color |  | PA66/Beige | PA66/Beige | PA66/Beige | PET/Beige | PAW/Black |
| Core-to-sheath area ratio |  | 7:3 | 3:7 | 7:3 | 3:7 | 5:5 |
| Color coordinates of core-sheath conjugate fiber | $L^*$ | 48.84 | 54.53 | 51.86 | 59.73 | 20.3 |
|  | $a^*$ | −5.08 | −3.14 | 0.16 | 0.54 | −0.83 |
|  | $b^*$ | 9.13 | 12.71 | −2.62 | 7.42 | 1.28 |
| Color coordinates of core one | $L^*$ | 41.2 | 41.2 | 43.93 | 43.93 | 18.03 |
|  | $a^*$ | −6.99 | −6.99 | −1.29 | −1.29 | −0.99 |
|  | $b^*$ | 4.12 | 4.12 | −7.74 | −7.74 | 1.94 |
| $\Delta E^*$ from core |  | 9.33 | 16.32 | 9.55 | 21.97 | 2.37 |
| Color coordinates of sheath alone | $L^*$ | 69.27 | 69.27 | 69.97 | 69.27 | 23.83 |
|  | $a^*$ | −6.78 | −6.78 | −6.18 | −6.78 | −0.88 |
|  | $b^*$ | 18.72 | 18.72 | 18.72 | 18.72 | 0.72 |
| $\Delta E^*$ from sheath |  | 22.63 | 16.33 | 28.40 | 16.50 | 3.57 |
| Core-sheath $L^*$ difference |  | 28.07 | 28.07 | 25.34 | 25.34 | 5.80 |
| Appearance evaluation |  | C | B | C | B | D |

As can be seen from the data in Tables 1 and 2, all of the core-sheath conjugate fibers of Examples 1 to 10 had color differences $\Delta E^*$ from the core part and from the sheath part of 3.0 or more, which means that a good appearance close to that of human hair was obtained. On the other hand, the core-sheath conjugate fiber for artificial hair of Comparative Example 1 did not have so much color difference from the core part and from the sheath part as with conventional core-sheath conjugate fibers for artificial hair, which means that a good appearance close to that of human hair was not obtained.

LIST OF REFERENCE NUMERALS

1 Core-sheath conjugate fiber for artificial hair (cross section)
10 Core part
20 Sheath part Although the disclosure has been described with respect to only a limited number of embodiments, those skilled in the art, having benefit of this disclosure, will appreciate that various other embodiments may be devised without departing from the scope of the present disclosure. Accordingly, the scope of the disclosure should be limited only by the attached claims.

The invention claimed is:

1. A core-sheath conjugate fiber for artificial hair comprising a core part and a sheath part,
wherein the core-sheath conjugate fiber for artificial hair is a colored fiber,
a color difference $\Delta E^*$ between the core-sheath conjugate fiber for artificial hair and the core part is 10 or more, and a color difference $\Delta E^*$ between the core-sheath conjugate fiber for artificial hair and the sheath part is 10 or more, and
the color difference $\Delta E^*$ is calculated by the following Equation (1) using CIE1976 (L* a* b*) color space:

$$\Delta E^* = [(L^*1 - L^*2)^2 + (a^*1 - a^*2)^2 + (b^*1 - b^*2)^2]^{1/2} \quad (1)$$

where L* represents lightness, a positive value of a* represents chromaticity toward red, a negative value of a* represents chromaticity toward green, a positive value of b* represents chromaticity toward yellow, a negative value of b* represents chromaticity toward blue, L*1, a*1, and b*1 are values for the core-sheath conjugate fiber for artificial hair and the core part, and L*2, a*2, and b*2 are values for the core-sheath conjugate fiber for artificial hair and the sheath part.

2. The core-sheath conjugate fiber for artificial hair according to claim 1, wherein the core part of the core-sheath conjugate fiber for artificial hair comprises, as a main component resin, one or more of polyester-based resins selected from the group consisting of polyalkylene terephthalate and a copolymerized polyester mainly containing polyalkylene terephthalate.

3. The core-sheath conjugate fiber for artificial hair according to claim 1, wherein the sheath part of the core-sheath conjugate fiber for artificial hair comprises, as a main component resin, a polyamide-based resin mainly containing at least one selected from the group consisting of Nylon 6 and Nylon 66.

4. The core-sheath conjugate fiber for artificial hair according to claim 1, wherein an L* value of the sheath part is larger than an L* value of the core part, and a difference between the L* value of the sheath part and the L* value of the core part is 30 or more.

5. A hair ornament product comprising the core-sheath conjugate fiber for artificial hair according to claim 1.

6. The hair ornament product according to claim 5, wherein the hair ornament product is one selected from the group consisting of a hair wig, a hairpiece, weaving hair, a hair extension, braided hair, a hair accessory, and doll hair.

7. A production method for the core-sheath conjugate fiber for artificial hair according to claim 1, comprising:
a step of melt spinning a core part resin composition and a sheath part resin composition, using a core-sheath conjugate nozzle.

8. The production method for the core-sheath conjugate fiber for artificial hair according to claim 7, wherein the core-sheath conjugate fiber for artificial hair is colored using three types of pigment masterbatches of black, red, and yellow.

9. The core-sheath conjugate fiber for artificial hair according to claim 1, having a concentric core-sheath structure.

10. The hair ornament product according to claim 5, wherein the core-sheath conjugate fiber for artificial hair has a concentric core-sheath structure.

11. The production method for the core-sheath conjugate fiber for artificial hair according to claim 7, wherein the core-sheath conjugate fiber for artificial hair has a concentric core-sheath structure.

* * * * *